(12) United States Patent
Bucevschi et al.

(10) Patent No.: US 6,833,488 B2
(45) Date of Patent: Dec. 21, 2004

(54) BIOCOMPATIBLE, BIODEGRADABLE, WATER-ABSORBENT MATERIAL AND METHODS FOR ITS PREPARATION

(75) Inventors: Mircea Dan Bucevschi, Rehovot (IL); Monica Colt, Rehovot (IL)

(73) Assignee: Exotech Bio Solution Ltd., Rehovot (IL)

( * ) Notice: Subject to any disclaimer, the term of this patent is extended or adjusted under 35 U.S.C. 154(b) by 379 days.

(21) Appl. No.: 09/823,612

(22) Filed: Mar. 30, 2001

(65) Prior Publication Data

US 2002/0193516 A1 Dec. 19, 2002

(51) Int. Cl.$^7$ .......................... A61F 13/16; C08G 63/48
(52) U.S. Cl. .................. 604/368; 525/54.1; 525/54.11; 525/54.4; 525/55; 525/63; 524/17; 524/18; 524/47; 604/372; 604/374
(58) Field of Search .............................. 525/54.1, 54.11, 525/54.4, 55, 63; 524/17, 18, 47; 604/368, 372, 374

(56) References Cited

U.S. PATENT DOCUMENTS

| | | | |
|---|---|---|---|
| 2,926,154 A | 2/1960 | Keim | 260/29.2 |
| 3,224,986 A | 12/1965 | Butler | 260/9 |
| 3,332,901 A | 7/1967 | Keim | 260/29.2 |
| 3,332,909 A | 7/1967 | Farnham | 260/47 |
| 3,395,099 A | 7/1968 | Johnson | 210/35 |
| 3,846,380 A | 11/1974 | Fujimoto et al. | 260/78 A |
| 3,926,869 A | 12/1975 | Horie et al. | 260/8 |
| 3,926,891 A | 12/1975 | Gross et al. | 260/29.6 |
| 3,935,099 A | 1/1976 | Weaver et al. | 210/43 |
| 3,959,569 A | 5/1976 | Burkholder, Jr. et al. | 428/475 |
| 3,980,663 A | 9/1976 | Gross | 206/29.6 |
| 3,997,484 A | 12/1976 | Weaver et al. | 260/17.4 |
| 4,060,081 A | 11/1977 | Yannas et al. | 128/156 |
| 4,076,633 A | 2/1978 | Edwards et al. | 252/8.75 |
| 4,076,663 A | 2/1978 | Masuda et al. | 260/17.4 |
| 4,076,673 A | 2/1978 | Burkholder, Jr. | 260/29.2 |
| 4,090,013 A | 5/1978 | Ganslaw et al. | 526/15 |
| 4,117,184 A | 9/1978 | Erickson et al. | 428/224 |
| 4,124,748 A | 11/1978 | Fujimoto et al. | 526/8 |
| 4,161,948 A | 7/1979 | Bichon | 128/156 |
| 4,176,677 A | 12/1979 | Hughes | 137/488 |
| 4,190,562 A | 2/1980 | Westerman | 260/17.4 |
| 4,264,493 A | 4/1981 | Battista | 260/117 |
| 4,286,082 A | 8/1981 | Tsubakimoto et al. | 526/240 |
| 4,349,470 A | 9/1982 | Battista | 260/117 |
| 4,389,513 A | 6/1983 | Miyazaki | 525/186 |
| 4,416,814 A | 11/1983 | Battista | 260/117 |
| 4,424,247 A | 1/1984 | Erickson | 428/138 |
| 4,435,172 A | 3/1984 | Gross | 604/368 |
| 4,459,068 A | 7/1984 | Erickson | 405/264 |
| 4,460,743 A | 7/1984 | Abe et al. | 525/68 |
| 4,465,039 A | 8/1984 | Snelgrove et al. | 123/142.5 |
| 4,497,930 A | 2/1985 | Yamasaki et al. | 524/556 |
| 4,525,527 A | 6/1985 | Takeda et al. | 524/831 |
| 4,590,241 A | 5/1986 | Hohlfeld | 525/132 |
| 4,654,039 A | 3/1987 | Brandt et al. | 604/368 |
| 4,666,983 A | 5/1987 | Tsubakimoto et al. | 525/119 |
| 4,734,478 A | 3/1988 | Tsubakimoto et al. | 527/300 |
| 4,780,505 A | 10/1988 | Mashita et al. | 525/66 |
| 4,808,637 A | 2/1989 | Boardman et al. | 521/50.5 |
| 4,833,222 A | 5/1989 | Siddall et al. | 526/200 |
| 5,118,719 A | 6/1992 | Lind | 521/92 |
| RE33,997 E | 7/1992 | Kuzma et al. | 523/106 |
| 5,284,936 A | 2/1994 | Donachy et al. | 530/350 |
| 5,385,983 A | 1/1995 | Graham | 525/330.1 |
| 5,408,019 A | 4/1995 | Mertens et al. | 526/240 |
| 5,447,727 A | 9/1995 | Graham | 424/487 |
| 5,453,323 A | 9/1995 | Chambers et al. | 428/402 |
| 5,567,478 A | 10/1996 | Houben et al. | 427/342 |
| 5,606,324 A | 2/1997 | Justice et al. | 342/62 |
| 5,612,384 A | 3/1997 | Ross et al. | 521/64 |
| 5,629,377 A | 5/1997 | Burgert et al. | 524/832 |
| 5,633,316 A | 5/1997 | Gartner et al. | 525/54.32 |
| 5,712,316 A | 1/1998 | Dahmen et al. | 521/72 |
| 5,733,576 A | 3/1998 | Chmelir | 424/488 |
| 5,736,595 A | 4/1998 | Günther et al. | 524/45 |
| 5,847,031 A | 12/1998 | Klimmek et al. | 524/44 |
| 5,847,089 A | 12/1998 | Damodaran et al. | 530/410 |
| 6,107,432 A | 8/2000 | Engelhardt et al. | 527/311 |

OTHER PUBLICATIONS

Chen, Jun et al., "Synthesis of superporous hydrogels: Hydrogels with fast swelling and superabsorbent properties." *J. Biomed. Mater. Res.* Jan. 1999;44(1):53–62.

Choi, H.S et al., "Volume Phase Transition Behavior of N–Isopropyl Acrylamide–N–Cyanomethyl Acrylamide Copolymer Gel Particles: The Effect of Crosslinking Density." *Journal of Applied Polymer Science*, vol. 72, pp.: 1091–1099 (1999).

(List continued on next page.)

*Primary Examiner*—Samuel A. Acquah
(74) *Attorney, Agent, or Firm*—Lahive & Cockfield, LLP

(57) ABSTRACT

A bio-compatible, biodegradable macromolecular water-absorbent polymeric material having a three-dimensional configuration with intermolecular covalent bonds and containing free functional groups selected from OH, SH, $NH_2$, and COOH. The polymer is formed by polymer-polymer inter-coupling interaction between a natural water-soluble polymer A or its derivatives having a molecular weight between 20,000 and 500,000 Da, and a synthetic polymer B in a ratio of A:B of 15:85 to 85:15. The natural polymer A can be selected from—a non-ionic natural, partially denatured or chemically modified polymer that does not dissociate in water and which can undergo polymer-polymer intercoupling reactions, or an anionic natural, partially denatured or chemically modified polymer, that dissociates in water to form anions and which can undergo polymer-polymer intercoupling reactions, —or a cationic natural, partially denatured or chemically modified polymer, that dissociates in water to form cations and which can undergo polymer-polymer intercoupling reactions or an amphoteric natural, partially denatured or chemically modified polymer, that dissociates in water to form both anions and cations and which can undergo polymer-polymer intercoupling reactions, or mixtures thereof.

31 Claims, No Drawings

OTHER PUBLICATIONS

Kiatkamjornwong, Suda et al., "Influence of Reaction Parameters on Water Absorption of Neutralized Poly(acrylic acid–co–acrylamide) Synthesized by Inverse Suspension Polymerization." *Journal of Applied Polymer Science*, vol. 72, pp.: 1349–1366 (1999).

Omidian, H. et al., Modified acrylic–based superabsorbant polymers (dependance on particles size and salinity) *Polymer*, vol. 40, pp.: 1753–1761 (1999).

Schwarte et al. "Novel poly (ethylene glycol)–grafted, cationic hydrogels: preparation, characterization and diffusive properties." *Polymer*, vol. 39, No. 24, pp. 6507–6066 (1998).

BIOCOMPATIBLE, BIODEGRADABLE, WATER-ABSORBENT MATERIAL AND METHODS FOR ITS PREPARATION

FIELD OF THE INVENTION

The present invention relates, generally, to composite materials comprised of intercoupled biopolymers and synthetic polymers, which when in contact with aqueous media behave as hydrogels, and methods for their preparation. More precisely, the present invention relates to the method of crosslinking three-dimensional macromolecular configurations by polymer-polymer intercoupling without using micromolecular or oligomeric combination crosslinking agents or coupling agent, in liquid media containing water. Most precisely, the invention relates to reacting synthetic polymers having reactive chemical functional groups with free chemical functional groups of biopolymers to form covalent bonds, without forming secondary products. The synthesis is preformed in a liquid-liquid heterogeneous system. Particularly, the invention relates to the preparation of superabsorbent materials that are biocompatible and biodegradable for use in different applications, such as for bodily hygiene, medical biomaterials, agromaterials, drying agents and others.

BACKGROUND OF THE INVENTION

Absorbing materials for water and aqueous solutions, including fluids, screted or eliminated by the human body are known. These materials are generally polymer based in the form of powders, granules, microparticles, films or fibres. Upon contact with aqueous liquid systems they swell by absorbing the liquid phase in their structure, without dissolving it. When the swelling reaches equilibrium there is obtaining a gel, which frequently is called "hydrogel".

These polymers (also referred to as superabsorbent polymers or hydrophilic resins) are primarily used in personal care products to absorb body fluids, for example baby diapers, adult incontinence products, feminine hygiene products, and the like. The hydrophilic resin particles quickly absorb fluids and retain such fluids to prevent leakage and give the absorbent structure a "dry feel" even when wetted.

In the applications for hygienic products, hydrophilic resin particles, as superabsorbent polymers, are incorporated into absorbent structures which contain for example, synthetic and natural fiber or paper based woven and nonwoven structures, and toughened masses of fibers, such as fluff pads. The materials used in such structures can quickly absorb aqueous fluids and distribute them over the whole absorbent structure. The structures, in the absence of hydrophilic resin particles, have limited absorption capacity, and are bulky due to the large amount of material needed to provide acceptable absorption capacity and do not retain fluid under pressure. Therefore, in order to improve the absorbency and fluid retention characteristics of such absorbent structures there are incorporated hydrophilic resin particles which imbibe fluids to form a swollen hydrogel material.

Initially, only the very high swelling capacity on contact with liquids, also referred to as free swelling capacity, had been the main factor in the development of superabsorbers; later it turned out, however, that not only the amount of absorbed liquid is of importance but also the stability of the swollen gel. As it turns out however, absorbency, also referred to as swellability or free swelling capacity, on the one hand, and gel strength of a cross-linked polymer, on the other hand, represent contradictory properties, as is known from U.S. Pat. No. Re 32,649. This means that polymers having a particularly high absorbency exhibit poor strength of the swollen gel so that the gel is deformable under pressure (e.g., the load of a body) and further liquid distribution and absorption is prevented. Therefore, a balance between absorption capacity (gel volume) and gel strength is to be aimed for to ensure liquid absorption, liquid transport, dryness of the diaper and the skin when such superabsorbers are used in a diaper structure. In this connection, not only the polymer's capability of retaining a liquid under pressure, after first swelling freely is of importance, but also that liquids be absorbed even when there exists a simultaneous pressure, i.e. while the liquid is being absorbed. This is the case in practice when a baby or person sits or lies on a sanitary article or when shear forces are exerted, such as by moving legs. This particular absorption property is referred to as absorption under load.

Furthermore, the absorbent capacity of superabsorbents for body fluids is dramatically lower than for deionised water. It is generally believed that this effect results from the electrolyte content of body fluids and the effect is often referred to as "salt poisoning".

Water absorption and water retention characteristics of superabsorbents are due to the presence in the polymer structure of ionisable functional groups. These groups are usually carboxyl groups, a high proportion of which are in the form of salt when the polymer is dry. and undergo dissociation and solvation upon contact with water. In the dissociated state, the polymer chain will have a series of functional groups having the same electric charge and thus repel one another. This leads to expansion of the polymer structure which, in turn, permits further absorption of water molecules. This expansion is, however, subject to the constraints provided by the cross-links in the polymer structure which must be sufficient to prevent dissolution of the polymer. It is assumed that the presence of a significant concentration of electrolytes in the water interferes with dissociation of the functional groups and leads to the "salt poisoning" effect. Although most commercial superabsorbents are anionic, it is equally possible to make cationic superabsorbents with the functional groups being, for example, quaternary ammonium groups. Such materials also need to be in salt form to act as superabsorbents and their performance is also affected by the salt-poisoning effect.

Superabsorbents have not found widespread use in superabsorbent sanitary articles used to absorb blood and other serous body fluids such as sanitary napkins, surgical wipes, because these superabsorbents do not absorb blood readily, since they do not have a high capacity for blood. Low blood absorbent capacity means that large amounts of the superabsorbent material must be incorporated in blood absorbent articles, which increases the cost of such articles.

Previously known processes for the production of in-situ superabsorbent polymers have the disadvantage that large amounts of monomers are present in an unreacted form after termination of the actual polymerization. Since these monomers are usually toxic, they are removed in a subsequent step by reacting them or otherwise. If reacted, they general form linear polymer chains of mean molecular weight and not the desired cross-linked polymers. These polymer chains are soluble and cannot contribute to the water absorption, in particular under load, or to the water retention under load. Furthermore, they have the undesired property of giving a slimy feel to the polymer after water absorption.

The known synthetic absorbers are practically water-insoluble, and although they absorb multiple amount of their weight of water, urine, or other aqueous solutions, they are relatively resistant to biodegradation.

Many strategies were used to increase the performance of superabsorbent materials such as:

chemical structure: partially neutralized poly(acrylic acid) polymer (see U.S. Pat. No. 4,654,039), partially neutralized copolymer of isobutylene and maleic anhydride (U.S. Pat. No. 4,389,513), a saponification product of a vinyl acetate-acrylic acid copolymer (U.S. Pat. No. 4,124,748), a hydrolyzate of acrylamide polymer or acrylamide copolymer (U.S. Pat. No. 3,959,569), a hydrolyzate of an acrylonitrile copolymer (U.S. Pat. No. 3,935,099), polysaccharides and its derivatives (U.S. Pat. No. 4,076,663, U.S. Pat. No. 4,076,663, U.S. Pat. No. 5,847,031; U.S. Pat. No. 5,712,316; U.S. Pat. No. 5,733,576; U.S. Pat. No. 5,736,595; U.S. Pat. No. 5,453,323, U.S. Pat. No. 6,107,432), proteins (U.S. Pat. No. 5,847,089, U.S. Pat. Nos. 4,264,493; 4,349,470; 4,416,814; U.S. RE33,997; U.S. Pat. No. 3,926,869; International Patent Publication WO 92/17525 and in U.S. Pat. No. 5,284,936) and composites materials with only synthetic polymers (U.S. Pat. No. 4,076,673; U.S. Pat. No. 3,224,986, U.S. Pat. No. 3,980,663, U.S. Pat. No. 3,997,484; U.S. Pat. No. 3,926,891;, U.S. Pat. No. 3,395,099; U.S. Pat. No. 4,090,013; U.S. Pat. No. 4,190,562; in U.S. Pat. No. 4,117,184; and U.S. Pat. No. 4,176,677) or synthetic polymers and natural polymers (U.S. Pat. No. 5,453,323, U.S. Pat. No. 6,107,432 or U.S. Pat. No. 5,847,089, U.S. Pat. Nos. 4,264,493; 4,349,470; 4,416,814);

formation of three dimensional configurations: polymerization only from monomers (U.S. Pat. No. 5,408,019; U.S. Pat. No. 4,076,663; U.S. Pat. No. 5,567,478; U.S. Pat. No. 5,629,377), polymerization from monomers, oligomers or/and polymers (U.S. Pat. No. 4,076,673, U.S. Pat. No. 3,224,986; U.S. Pat. No. 3,980,663; U.S. Pat. No. 4,424,247; in U.S. Pat. Nos. 3,997,484; 3,926,891; 3,395,099; 4,090,013; and 4,190,562; in U.S. Pat. Nos. 2,926,154; 3,224,986; and 3,332,909; U.S. Pat. Nos. 2,926,154; 3,224,986; and 3,332,901; U.S. Pat. No. 4,435,172; U.S. Pat. No. 4,459,068; U.S. Pat. No. 5,612,384 and crosslinking with micromolecular or oligomeric auxiliary, usually bifunctional, by ionic reaction mechanism, with or without forming secondary products and without generating structural polymer fragments during the chemical process. (U.S. Pat. No. 5,612,384; U.S. Pat. No. 3,846,380; U.S. Pat. No. 3,926,869; U.S. Pat. No. 4,161,948; U.S. Pat. No. 4,060,081; U.S. Pat. No. 5,385,983; U.S. Pat. No. 5,447,727; U.S. Pat. No. 4,666,983; U.S. Pat. No. 4,734,478 U.S. Pat. No. 4,497,930 and U.S. Pat. No. 4,833,222). The synthesis methods used have the disadvantage that the three-dimensional network generated, beside the fact that the "eyes" are too big, have the ionizable chemical functions attached at the network by very short segments, which can't compensate the mechanical effort at which are subdued the hydrogels during uses.

It is also possible to form three-dimensional structures by polymer-polymer reactions. This method has been met at reactive processing of synthetic polymers in melting stage (Xanthos M. "Reactive Extrusion"-Hanser Publishers, New York, 1992 and for example U.S. Pat. No. 4,460,743; U.S. Pat. No. 4,590,241; U.S. Pat. No. 4,780,505).

chemical processes technology for three-dimensional macromolecular configuration: aqueous solution (U.S. Pat. Nos. 4,465,039; 4,076,633; 4,286,082; and 4,525, 527), aqueous suspensions (U.S. Pat. No. 5,847,031; U.S. Pat. No. 5,447,727; Omidian H., Hashemi S. A., Sammes P. G., Meldrum I., "Modified acrylic-based superabsorbent polymers, dependence on particle size and salinity", Polymer, 40, 1753–1761,1999), and emulsions (U.S. Pat. No. 5,633,316; U.S. Pat. No. 4,808,637; U.S. Pat. No. 4,076,673; U.S. Pat. No. 5,629,377; Schwarte L. M., Peppas N. A., "Novel poly(ethylene glycol)-grafted, cationic hydrogels: preparation, characterization and diffusive properties", Polymer, 39, 6057–6066, 1998). These have the disadvantage that monomers and oligomers used for polymeric network synthesis can not be completely converted in reaction products and remain in finite product as "extractible" materials. Unconsumed reactants diminishing the imposed properties by the users of the superabsorbent materials with concrete reference to decreasing of absorbency and of the absorbency under load (AUL). Also, the unconsumed substances in the chemical processes are extracted by biological fluids and in contact with the organism caused toxic effects.

processing of reaction mass to obtain solid material: synthesis in aqueous media, by drying (U.S. Pat. No. 5,612,384; U.S. Pat. No. 3,846,380; U.S. Pat. No. 3,926,869 U.S. Pat. Nos. 4,465,039; 4,076,633; 4,286, 082; and 4,525,52).

Considering the diminishing of the "gel blocking" effect, patents (U.S. Pat. No. 5,385,983; U.S. Pat. No. 5,447,727; U.S. Pat. No. 5,606,324) use the crosslinking post-synthesis, which occurs in a second phase of drying at temperatures higher than 120° C. The disadvantages of these methods of reaction mass processing consist in that they induce an intense shrinking of the three-dimensional network, which favors the formation of hydrogen bonds, which can't be destroyed on the contact with aqueous liquid media and in consequence, decreasing of absorbency.

It is known from U.S. Pat. No. 5,118,719 to produce superabsorbent polymers having improved rate of water absorption by means of carbonate-containing blowing agents which, by releasing carbon dioxide, result in a hydrogel having a microcellular structure. As can be seen in the examples of U.S. Pat. No. 5,118,719, the absorption rate is improved, however, the absorption capacity reduced. Absorbent resins manufactured according to U.S. Pat. No. 5,118,719 have a considerably poorer absorption under load (AUL). The research papers such as (Chen J., Park H., Park K., "Synthesis of superporous hydrogels: Hydrogels with fast swelling and superabsorbent properties", J.Biomed.Mater.Res, 44,53–62,1999) mention the importance of polymer particles' porosity that followed to be used as superabsorbent. The known processes for inducing porosity in superabsorbent polymeric materials is disclosed in: phase inversion (Choi H. S., Kim M. J., Lee K. J., Bae Y. C., "Volume phase transition behavior of N-isopropyl acrylamide-N-cyanomethyl acrylamide copolymer gel particles: The effect of crosslinking density", J.Appl.Polym.Sci., 72,1091–1099,1999; Kiatkamjornwong S., Phunchareon P., "Influence of reaction parameters on water absorption of neutralized poly(acrylic acid-co acrylamide) synthesized by inverse suspension polymerization", J.Appl.Polym.Sci., 72, 1349–1366, 1999) or freeze drying (Shiga T., Hirose Y., Okada A., Kurauchi T., "Bending of poly(vinyl alcohol)-poly(sodium acrylate) composite hydrogel in electric fields", J.Appl.Polym.Sci., 44, 249–253,1992)

Superabsorbents that are biodegradable are disclosed in U.S. Pat. No. 5,712,316; U.S. Pat. No. 5,733,576; U.S. Pat.

No. 5,736,595. U.S. Pat. No. 5,847,089, and U.S. Pat. Nos. 4,264,493; 4,349,470; 4,416,814. The performances of these materials, however, are low owing to the long time of initiation of biochemical process of degradation.

The only way to meet the increasing trend of reducing the size and thickness of sanitary articles for esthetic and environmental reasons (reduction of waste in the land fill) is to reduce the large-volume fluff pulp portion in diapers, adult incontinence products, feminine hygiene products, and the like, and to increase the portion of superabsorbent at the same time. For that reason the superabsorbent has to take over additional functions with respect to liquid absorption and transport thereof, which were previously performed by the fluff pulp and which cannot be accomplished by the known superabsorbents to a satisfactory extent.

DESCRIPTION OF THE INVENTION

Ii is an object of the present invention to provide substantially improved superabsorbent polymers by using a new type of composite material based on the interaction of a natural polymer and a synthetic polymer.

Another object of the invention is to provide a new type of macromolecular three-dimensional configuration by polymer-polymer intercoupling reactions between proteinaceous and/or polysaccharidic biopolymers and reactive synthetic polymers.

A further object is to provide superabsorbents containing natural polymers that confer an improved biocompatibility on contact with human body.

Another object of the present invention is to provide new water-absorbing hygienic products able to biodegrade in natural medium after use.

A further object of the present invention, is to provide a new water-absorbing material having improved absorption and absorption rate at contact with respect of biological fluids such as urine and blood comprising amphoteric polymers with anticoagulant properties.

Another object of the invention is to provide a method of preparing a new type of superabsorbent polymer composition with superior absorbency and higher absorbency rate, by polymer-polymer intercoupling a reactive synthetic polymer having reactive ionic chemical groups with a biopolymer.

Yet another object of the present invention is to provide a method of preparing new water-absorbing materials in a liquid-liquid heterogeneous system at ambient temperature with reduced energy consumption compared with known processes.

Particularly, the polymers of the present invention provide improvement of absorption and retention under load (AUL) by reacting the mass via phase inversion which provides a porous structure of the resultant solid when drying in vacuum at a temperature technologically accessible.

The process of preparing the water-absorbing material of the present invention avoids the toxic effect because of the formation of a three-dimensional network between functional groups that lead at covalent bonds without been accompanied by secondary products of reaction.

DETAILED DESCRIPTION OF THE INVENTION

The biocompatible and biodegradable water-absorbing material (WAM), which is the object of this invention, is a composite material.

The term "composite material" used hereinafter, refers to a macromolecular product having a three-dimensional configuration, with intermolecular covalent bonds formed by polymer-polymer intercoupling reactions.

This term also includes a mixture of such a macromolecular product and other compounds providing special properties, such as biologically active compounds (i.e. drugs, stimulators, inhibitors, or anticoagulants, odorants, emollients, fertilizers, pesticides and others) when used in potential applications with water-absorbing material.

The composite material of the invention is a biocompatible, biodegradable macromolecular water-absorbent polymeric material having a three-dimensional configuration with intermolecular covalent bonds and containing free functional groups selected from OH, SH, $NH_2$, and COOH, said polymer being formed by polymer-polymer intercoupling interaction between a natural water-soluble polymer A or its derivatives having a molecular weight between 20,000 and 500,000 Da, and a synthetic polymer B in a ratio of A:B of 15:85 to 85:15, wherein the natural polymer A is selected from:

A1)—non-ionic natural, partially denatured or chemically modified polymer, that does not dissociate in water and which can undergo polymer-polymer intercoupling reactions, having only free hydroxyl groups in an amount of at least $5 \times 10^{-3}$ moles OH/g, and optionally containing non-ionic groups, A2)—anionic natural, partially denatured or chemically modified polymer, that dissociates in water to form anions and which can undergo polymer-polymer intercoupling reactions, said polymer optionally containing non-ionic groups, A3)—cationic natural, partially denatured or chemically modified polymer, that dissociates in water to form cations and which can undergo polymer-polymer intercoupling reactions, said polymers optionally containing non-ionic groups, A4)—amphoteric natural, partially denatured or chemically modified polymer, that dissociates in water to form both anions and cations and can undergo polymer-polymer intercoupling reactions, and A5)—mixtures of A1–A4, polymer A being capable of undergoing polymer-polymer intercoupling, and wherein:

synthetic polymer B is a linear or branched reactive synthetic copolymer having a molecular weight of 10,000–500,000 Da derived from a vinyl monomer and an ethylenically unsaturated monomer, said copolymer having a backbone with polymeric subunits $R_n$ and $R_r$, wherein R represents a subunit covalently bonded to the polymer backbone, n represents non-reactive chemical functional groups and r represents reactive chemical functional groups.

More precisely, the unique polymeric material of this invention is formed from N number of polymers that are polymer-polymer intercoupled, with N=2, 3 or 4. Of these N polymers, (N-1)=K polymers comprise polymer A and polymer B is comprised of N-K polymers.

Polymer A represents biopolymers. The structure of the biopolymers that enables them to undergo polymer-polymer intercoupling reactions is the presence of certain free chemical functional groups, symbolized "u" these groups are: —OH; —SH; —$NH_2$ and —COOH.

The biopolymers A of the present invention are preferably proteins, glycoproteins, polysaccharides or proteoglycans of animal, vegetal or bacterial origins. Preferably polymers A is preferring are biopolymers or their derivatives mentioned above that are soluble in water or aqueous solutions and have an average molecular weight not less than 20,000 Da and not more than 500,000 Da. Preferably, polymer A can be categorized as one of the following depending on its functional groups:

1) A1—non-ionic, where K=1.

with only hydroxyl functions, symbolized as "$f_{OH}$", comprising at least $5 \times 10^{-3}$ moles OH/g. Representative polymers of this group are starch, amylose, dextran, chitin, pullulan, gellan gum, xylan, galactomannan, carrageenan, agar, locust bean gum, guar gum, gum arabic, pectin, and respectively: methylcellulose, ethylcellulose, hydroxyethylcellulose, hydroxypropyl-cellulose, ethylhydroxyethylcellulose, hydroxybutylmethylcellulose, hydroxyethylmethylcellulose, hydroxyethyl starch, hydroxypropyl starch and other similar products.

2) A2—anionic (when K=2).

with carboxylic functions, symbolized as "$f_{cooH}$," having at least $1 \times 10^{-3}$ moles COOH/g. Polymers in this category include alginate, xanthan, hyaluronic acid, heparin, chondroitin sulfate, keratan, dermatan, oxidized cellulose, carboxymethylcellulose or carboxymethyl starch.

3) A3—cationic (when K=1).

With primary amino functions, symbolized as "$f_{NH2}$", having at least $0.5 \times 10^{-3}$ moles $NH_2$/g. representative of the A3 polymers are—chitosan and other polysaccharides which include in their structure glycosamines residues, in natural or diacetylated form.

4) A4—"amphoteric-(when K=1).

With primary amino functions, with a functionality $f_{NH2}$ of at least $0.5 \times 10^{-3}$ moles $NH_2$/g and carboxylic functions, with a functionality $f_{cooH}$ of at least $1 \times 10^{-3}$ moles COOH/g, with isoelectric point (IEP) not less than 2.5 and not more than 10.5. The most preferable amphoteric biopolymers A4 are: collagen, collagenic biopolymers (atelocollagen, solubilized collagen, gelatin and collagen hydrolysate) products from terrestrial and marine sources and derivatives of those, -alfa-keratose, gama-keratose, keratin hydrolysate and derivatives of the elastinic biopolymers, fibrin and derivatives, fibroin and derivatives, ovalbumine, bovine serumalbumine and albumine derivatives, casein and its derivatives, soybean protein and its derivatives, heparosan, hyalurosan and other similar diacetylated glycosaminoglycans.

5) A5—(when K=2 or 3).

where the mixture of two biopolymers (K=2) is represented by AX:AY, with AX having a value from 1 to 99 percent by weight, where AX and AY are different biopolymers from the groups A1 to A4. The composition of a ternary (K=3) mixture is represented by AX:AY:AZ with the value for AX and AY being from 1 to 98 percent by weight, the rest being AZ, where AX, AY and AZ are different biopolymers from groups A1 to A4. Preferred are the proteins and polysaccharide mixtures, which have chemical functionalities suitable for participating in polymer-polymer intercoupling similar to the polymers of group A4.

Especially preferred are the biopolymers and their derivatives accepted by the pharmaceutical industry and which are commercially available, such as: collagen and collagenic biopolymers, keratin hydrolysates, fibrin, casein, soybean protein, starch, dextran, alkyl and hydroxyalkylcellulose, carboxymethylcellulose, carboxymethyl starch, hyaluronic acid, chondrotin sulfate A, heparin, chitin and chitosan.

Polymer B is a synthetic polymer. Preferably it is a reactive linear or branched synthetic copolymer obtained either via single stage chemical processing, such as polymerization, polycondensation, etc., or via a two stage polyreaction process, followed by chemical modification (known as "polymer-analogous transformations").

The reactivity of polymer B enabling it to udergo polymer-polymer intercoupling is due to certain types of functional groups, one of which is a reactive chemical function, symbolized by "r", in comparison with free chemical functions of the biopolymers, as well as a non-reactive chemical function, symbolized by "n", which can not react with covalent bonds.

The most preferred reactive synthetic copolymers B have an average molecular weight not less than 10,000 Da and not more than 500,000 Da and have reactive chemical functions in the form of reactive substituents, symbolized as "R-r", and non-reactive substituents, symbolized as "R-n", where R is a chemical group attached by covalent bonds to the backbone atoms or braches of the backbone of the synthetic polymers. R may be itself a reactive or non-reactive chemical group, and may contain another group, known as a "spacer", which is interposed between the chemical function and the chain that is anchored to this one. The chemical structures of preferred spacers are —CO—O— and —$(CH_2)_n$— with n equal from 1 to 4.

From the great number of different known types of reactive chemical functions that can participate in polymer-polymer intercoupling reactions, the present invention prefers polymers with groups that intervene in the chemical process by ionic mechanism. More preferred, in accordance with the invention's goal, are those reactive chemical functions that aren't accompanied by secondary products, with the occasion of a covalent bond's forming. The most preferred ionic reactive chemical functional groups are represented by —CO—O—CO— and —CO—NH—CO—, such as: maleic anhydride, itaconic anhydride, citraconic anhydride, 2-octenylsuccinic anhydride and respectively, the adequate imides. Particularly preferably are: maleic anhydride and itaconic anhydride.

In the context of the present invention, it is accepted that the non-reactive substituents on the polymer B belong to at least "m" number of different structural types, with m=1, 2, 3 or 4, preferably m=1 or 2. Preferred non-reactive substituents are: hydrogen, aliphatic or aromatic hydrocarbonate residues with 1–20 carbon atoms, non-activated esteric groups, etheric, iminic or non-activated halogenated derivatives. Optionally, under specific reaction conditions of polymer-polymer intercoupling, the non-reactive substituent may be represented by atomic groups, as such, or only part of these, that represent polar chemical functions, for instance, hydroxyl, amino, amido or carboxylic groups.

In accordance with the present invention, it is preferred that non-reactive substituents be attached of backbone of the copolymer, that represent monomer residues. The most preferred categories of monomers, carrying the non-reactive substituents are: styrene, alpha-methylstyrene, alkylated styrenes such as ethylstyrene or tert-butylstyrene, vinyltoluene, vinyl esters of saturated $C_1$–$C_4$-carboxylic acids such as vinyl formate, vinyl acetate or vinyl propionate, alkyl vinyl ethers with at least 2 carbon atoms in the alkyl group, such as ethyl vinyl ether or butyl vinyl ether, acrylate or methacrylate esters such as 2-ethylhexyl acrylate, n-butyl acrylate, isobutyl acrylate, t-butyl acrylate, hexyl acrylate, n-butyl methacrylate, lauryl methacrylate and isodecyl methacrylate; conjugated diolefins such as butadiene, isoprene, and piperylene; allenes such as allene, methyl allene and chloroallene; olefin halides such as vinyl chloride, vinyl fluoride and polyfluoro-olefins, ethylene, propene, isobutylene, butadiene, isoprene, esters of mono-ethylenically unsaturated $C_3$–$C_6$-carboxylic acids, i.e. esters of monohydric $C_1$–$C_8$-alcohols and acrylic acid, methacrylic acid or maleic acid, monoesters of maleic acid, i.e. monomethyl maleate, and hydroxyalkyl esters of said monoethylenically unsaturated carboxylic acids, i.e. 2-hydroxyethyl acrylate, hydroxypropyl acrylate, hydroxybutyl acrylate, hydroxyethyl methacrylate, hydroxypropyl methacrylate and hydroxybutyl methacrylate, N-vinyllactams such as N-vinylpyrrolidone or N-vinylcaprolactam, acrylic and methacrylic esters of alkoxylated monohydric saturated alcohols, vinyl pyridine and vinyl morpholine, N-vinylformamide, dialkyldiallylammonium halides such as dimethyldiallylammonium chloride, diethyldiallylammonium chloride, allylpiperidinium bromide, N-vinylimidazoles such as N-vinylimidazole, 1-vinyl-2-methylimidazole and N-vinylimidazolines such as N-vinylimidazoline, 1-vinyl-2-methylimidazoline, 1-vinyl-2-ethylimidazoline or 1-vinyl-2-propylimidazoline, acrylamide, methacrylamide or acrylonitryl.

Particularly preferable are: ethylene, propene, styrene, isobutylene, vinyl acetate, methyl acrylate, methyl methacrylate, acrylamide, vinylether, N-vinylpyrrolidone, acrylic acid, methacrylic acid or maleic acid.

Optionally, the non-reactive substituent may be represented by a reactive chemical function, consumed before the polymer-polymer intercoupling reaction is completed by "special combinations", using known methods of coupling.

The reactive ionic functional group of polymer B, symbolized by $f_r^B$, is preferably not less than $5 \times 10^{-3}$ moles "r"/g and not more than $1 \times 10^{-2}$ moles "r"/g.

Especially preferred are the reactive synthetic polymers accepted by the pharmaceutical industry and which are commercially available. For example, among the ionic reactive chemical function are: poly (ethylene-alt-maleic anhydride), poly(ethylene-graft-maleic anhydride), poly (isobutylene-co-maleic anhydride), poly(isoprene-graft-maleic anhydride), poly(maleic anhydride-co-1-octadecene), poly(propylene-graft-maleic anhydride), poly (styrene-co-maleic anhydride), etc.

The term "polymer-polymer intercoupling", refers to the chemical process, possibly from a thermodynamic point of view, of forming cavalent bonds, which occur between a number of N polymers with different macromolecular structures, through chemical functions that every polymer possesses and without the intervention of any micromolecular substance, such as a crosslinking agent or coupling agent.

The polymer-polymer intercoupling reaction is exemplified in FIG. 1 for a system using two reactants, polymer A and polymer B.

The intercoupling reactions between different types of polymers A and B having various reactive chemical functions, preferred in this invention, are shown in symbolized mode in FIG. 2.

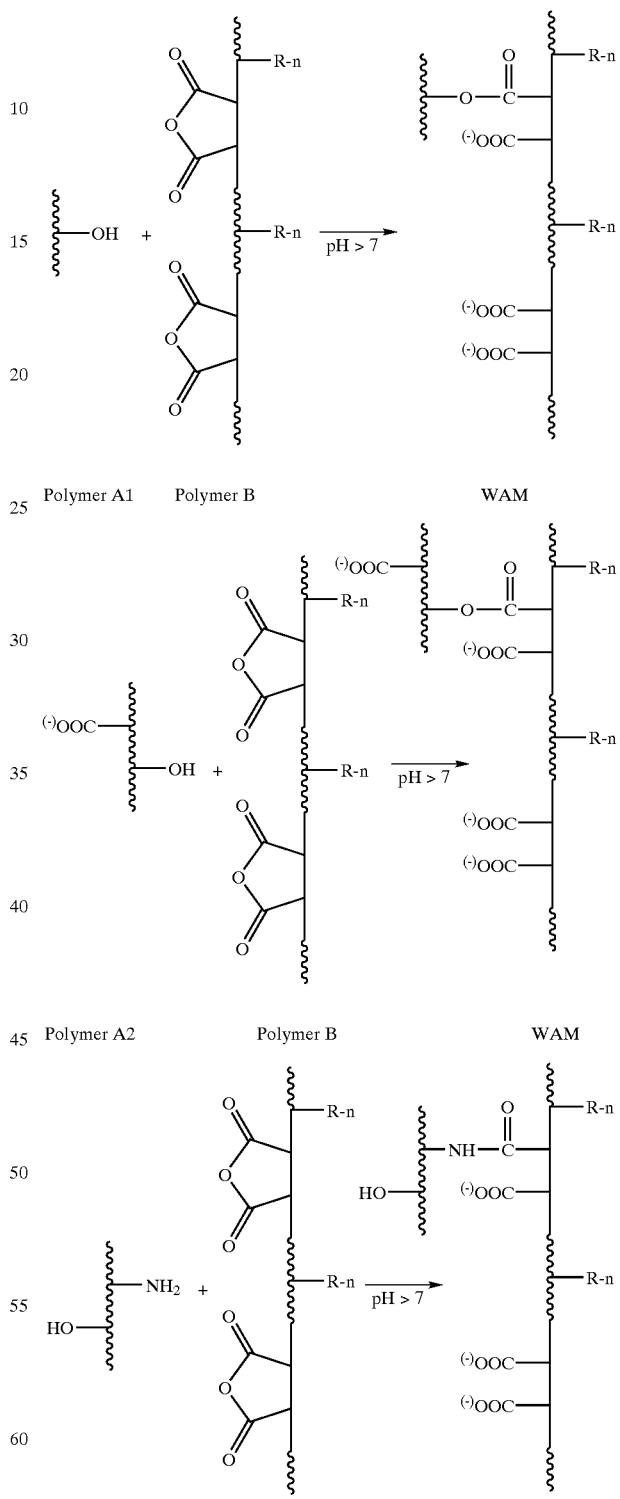

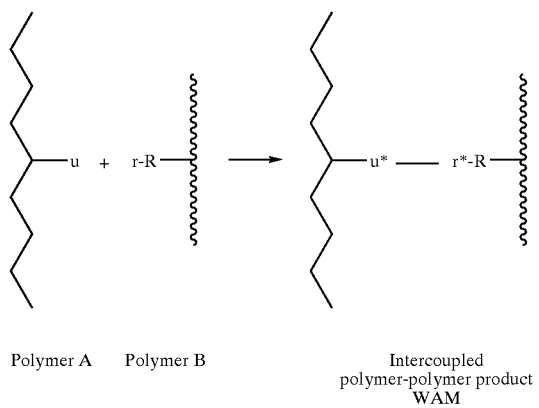

Polymer A    Polymer B        Intercoupled
                              polymer-polymer product
                              WAM u - free chemical function
r - reactive chemical function
u* - modified free chemical function
r* - modified reactive chemical function

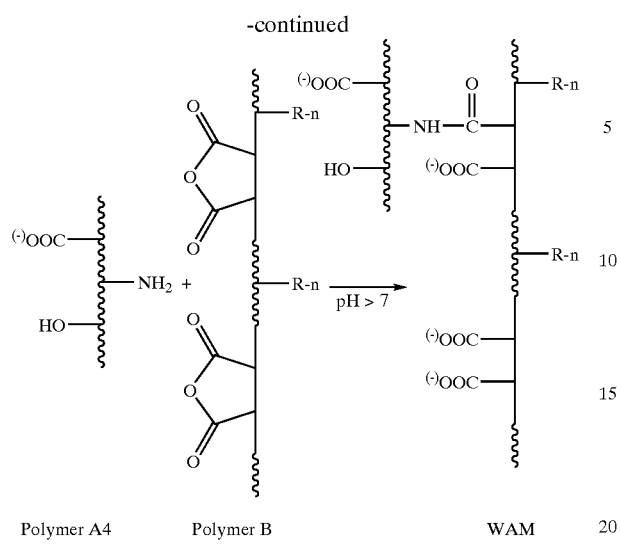

Polymer A4  Polymer B  WAM

The polymer-polymer intercoupling between reactant polymer A and reactant polymer B, which is the objective of the present invention, occurs in heterogeneous system.

FIG. 3 presents a three-dimensional model of the structure of a polymer-polymer intercoupling reaction product between reactant polymer A and reactant polymer B, that explains the performance of the water-absorbent material (WAN).

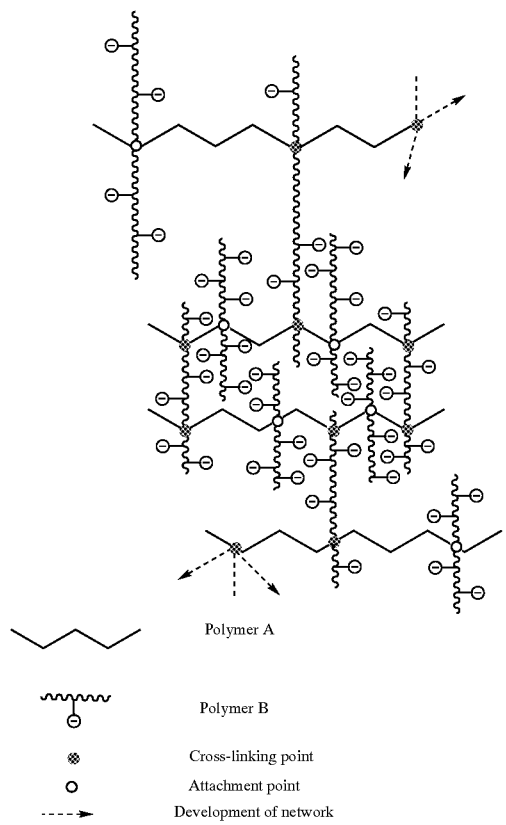

Polymer A
Polymer B
⊗ Cross-linking point
○ Attachment point
---▶ Development of network

Preparation of Water Absorbent Material (WAM) in Liquid-liquid Heterogeneous System

By the term "liquid-liquid heterogeneous system" is meant a material volume resulting from liquid components that immediately after preparing has the specific properties of liquids, and when not under shear stress, presents two distinct phases, delimited by a contact interface (similar to the mixture of two non-miscible or partially miscible liquids, known as emulsion).

The liquid-liquid heterogeneous process of polymer-polymer ginter-coupling, that is the objective of this invention, consists of four steps:

a) preparation of intermediary liquids, (L1), (L2) and (L3);
b) preparation of biopolymer reaction liquid LA and synthetic polymer reaction liquid LB;
c) polymer-polymer intercoupling by mixing liquids LA and LB;
d) processing the intercoupled reaction mass, with a view of separating the reaction product as water-absorbing material (WAM).

1) Preparation of Intermediary Liquids i) The Intermediary Liquid L1

A suitable amount of solid biopolymer A, selected from polymer types A1, A2, A3 or A4 is dissolved in a volume of water with a conductivity less than 10 $\mu$S, by simply mixing the two components in adequate ratios to obtain solutions of concentration not less than 1% and not more than 20%, preferably between 2% and 10%. The resulting solution being represented as L1.

ii) The Intermediary Liquid L2

A quantity of solid reactant polymer B is dissolving in a volume of organic solvent by simply mixing the two components in adequate ratios so that to obtain solutions of concentration not less than 1% and not more than 20%. The most preferred polymer solutions contain reactive synthetic polymers in concentrations of not less than 2% and not more than 10%. The resultant solution being represent as L2.

By the term "organic solvent," in this invention, is meant a homogeneous mixture of organic liquids $OL_1$ and $OL_2$. The ratio of $OL_1:OL_2$ being from 85:15 to 100:0, expressed in weight percent. The most preferred ratios are $OL_1:OL_2$ from 92:8 to 100:0, expressed in weight percent.

The organic liquid $OL_1$, according to this invention, preferably has a solubility in water not less than $10^3$ ppm and not more than $10^5$ ppm (according to the data of the solubility in water of the organic substances from YAWS C. L., "Chemical Properties Handbook", McGraw-Hill Companies Inc., New York, 1999) and which is a non-solvent for biopolymer A. The most preferred organic substances are: ethyl acetate, dichloromethane, 1,2-dichloroethane, methyl chloride, 1,1,1-trichloroethane or trichloroethylene. Particularly preferred are ethyl acetate and 1,2-dichloroethane.

The organic liquid $OL_2$ useful in this invention is preferably an aprotic dipolar solvent such as: N,N'-dimethylformamide (DMF), N,N'-dimethylacetamide (DMA) or dimethylsulphoxide (DMSO). The most preferred is N,N'-dimethylformamide.

iii) The Intermediary Liquid L3

A suitable amount of a base is dissolved in a volume of water with a conductivity less than 10 $\mu$S, by simply mixing the two components in adequate ratios so as to obtain solutions having a base concentration not less than 2% and not more than 20%, preferably between 4 and 8%. The resulting solution represents the intermediary liquid L3.

The base is preferably lithium hydroxide, sodium hydroxide, potassium hydroxide, ammonium hydroxide, lithium carbonate, lithium bicarbonate, sodium carbonate, sodium bicarbonate, potassium carbonate, potassium bicarbonate and ammonium bicarbonate. They can be used individually or preferable as mixtures.

2) The Preparation of Reaction Liquids i) The Reaction Liquid LA

When N=2, L1 is mixed with an amount of L3, so that to result in a solution having a pH, namely "pH of polymer-polymer intercoupling reaction", (pH$^{pp}$), not less than 7.5 and not more than 9.5, preferably between 8 and 9. The obtained solution is called biopolymeric reaction liquid LA.

When N>2, two or more solutions of biopolymer, each of them prepared from a different reactant A, but belonging of the one type from A1 to A4, according to the method described for L1, namely L1$_x$; L1$_y$ respectively, L1$_z$, x≠y≠z, x;y;z=1;2;3 or 4, each of them is mixing with a quantity of L3, to result in a solution with the same pH value (pH$^{pp}$), not less than 7.5 and not more than 9.5, preferably with values between 8 and 9. The obtained solutions are called LA$_x$; LA$_y$ respectively, LA$_z$.

Furthermore, two or three solutions LA$_x$; LA$_y$ and LA$_z$, respectively, may be mixed with ratios of LA$_x$:LA$_y$ or LA$_x$:LAy:LA$_z$ similar to composite reactant A5. The resulting composite solution being called CLA.

ii) The Reaction Liquid LB

A quantity of liquid L2 is added to a quantity of water with a conductivity less than 10 µS, by simply mixing the two components, in adequate proportions so that the ratio L2:W is not less than 90:10 and not more than 99:1, preferably between 94:6 and 97:3. The resulted composition is called reaction liquid LB.

3) The Polymer-polymer Intercoupling

Into a reaction vessel equipped with a stirring rod of anchor type with four blades, thermostatic jacket, condenser, thermometer, dropping funnel and electrode for pH monitoring, connected to an automated titroprocessor, is introducing a quantity of LB and homogenizing at a speed not less than 50 rpm and not more than 350 rpm, preferably between 100 rpm and 200 rpm, until the liquid reaches a temperature not less than 15° C. and not more than 35° C., preferably between 20° C. and 30° C. At the same time there is inserted in the dropping funnel is inserting a quantity of L3, necessary to adjusted the pH of liquid-liquid heterogeneous system during the polymer-polymer intercoupling reaction. The automated titroprocessor is then started and a quantity of LA is added in kneader so as to form a reaction mass, called RM, in which the reactant A represents not less than 15% and not more than 85%, expressed in weight percent, based on polymeric composite A+B. The automated titroprocessor is adjusted to a precision to maintain the system's pH at a constant value of pH$^{pp}$=±0.1 pH units.

Further, RM is stirred at a constant speed range and temperature maintained at the values mentioned above, noting the time of evolution of the variation rate of the system's pH, ΔpH/Δt, where:

$$\Delta pH = pH_{RM}^{PP} - pH_{RM}^{mod} = 0.1 \quad (1)$$

wherein:

pH$^{pp}$, represents the pH value at which was choose to make the polymer-polymer intercoupling reaction;

pH$^{mod}$, represents the pH value at which RM attains at one time, owing to the chemical processing which are specific for polymer-polymer intercoupling and is necessary the correction of the value by adding of L3, so that to come back at the value corresponding to pH$^{pp}$, and $$\Delta t = t_{reaction}^{pH^{mod}} - t_{reaction}^{pH^{PP}} \quad (2)$$

wherein:

$t^{pH^{pp}}$ represents the time of polymer-polymer intercoupling reaction, when the pH of RM has the value which has been adopted for synthesis;

$t^{pH^{mod}}$ represents the following time of polymer-polymer intercoupling reaction when pH of RM attains the value pH$^{mod}$ and necessitated its correction.

The polymer-polymer intercoupling reaction in liquid-liquid heterogeneous system is considered that is finished when the variation rate of the system's pH attains the value ΔpH/Δt=0.1/60=0.001667 pH units/minute.

When the stirring is stopped the reaction mass, called RM$^L$ represents a two-phase system. One of the phases is viscoelastic and transparent, which is referred to as "crude gel", CG and is the polymer-polymer intercoupling reaction's product in the swollen state with a liquid rich in water content. The other phase is a material without consistency and transparency, with rheological characteristics similar to the liquids, which are referred to as "crude residual liquid", CRL.

4) The Processing of Reaction Mass

At the end of the chemical reaction, the two-phase reaction mass is treated with liquid L3, so that the reaction mass attains a pH, called "the pH of water-absorbing material", pH$^{(WAM)}$, with a value not less than 6.5 and not more than 9, preferably between 7 and 8. After adjusting the pH, the reaction mass is separated by centrifugation with the following technological parameters: a) temperature, not less than 25° C. and not more than 45° C., preferably between 30° C. and 40° C.; b) speed, not less than 1,500 rpm and not more 3,000 rpm, preferably between 2,000 and 3,000 rpm; c) time, not less than 4 minutes and not more than 10 minutes, preferably between 6 and 8 minutes. The liquid phase, called "centrifugated crude residual liquid", CCRL, is decanted.

The sediment, called "centrifugated crude gel", CCG, having a mass "m$_G$" is put in a profiling device of syringe type, formed from a cylinder and a piston made from polytetrafluoroethylene, equipped with discharging spout with a cylindrical section of diameter "d$_F$" not less than 0.2 mm and not more than 2 mm, preferably between 0.7 and 1.5 mm. The profiling syringe is immersed, with the discharging zone, into an organic liquid mass, called "non-solvent" (NS), "m$_{NS}$" which is stirred, with a flowing regime Re, with a value not less than 8,000 and not more than 22,000, preferably between 14,000 and 16,000, (to induce an effect of sectioning of gel thread), so that the ratio m$_G$:m$_{NS}$ will have value not less than 1:2 and not more than 1:6, preferably between 1:3:5 and 1:4:5. The spinning flow of gel mass "D$_G$" is adjusted to a value not less than 10 g/minute and not more than 100 g/min, preferably between 40 and 70 g/minute.

The term "non-solvent", in accordance with the present invention, means an organic liquid that can not dissolve the polymeric compounds from the reaction mass, but has a solubility in water, OL1 and OL2 greater than 10$^6$ ppm. The preferred "non-solvent" organic liquids are: acetone, 1,4-dioxan, methyl alcohol, ethyl alcohol and tetrahydrofuran. The most preferably non-solvents are acetone and ethyl alcohol.

After profiling, the granules are maintain in non-solvent for not less than 60 minutes and not more than 240 minutes, preferably 90 minutes, under the same stirring conditions, filtered under vacuum and washed with adequate volumes of non-solvent, until, in the washing liquid is no longer identified in the organic liquid OL1 and OL2.

At the end, the wet granular mass is dried under vacuum at a temperature not less than 40° C. and not more than 70° C., preferably between 50° C. and 60° C., until the moisture content of the dried solid is no more than 10%, preferably 7%.

The resulting dried solid is broken up into small pieces in a mill with knifes to obtain granules with an average particle size not less than 0.1 mm and not more than 1.5 mm. The granular product after milling represents the water-absorbing material (WAM), which has a structure shown in FIG. 3.

Samples of WAM where tested in accordance with the procedure outlined, which follows.

METHODS OF ANALYSIS AND TESTING

Percent Moisture (U.S. Pat. No. 5,629,377)

The percent moisture values reported herein are defined as the percent weight loss of a 10 g sample of ground resin in a circulating air oven at 105° C. over 3 hours. Additional weight loss during pre-treatment was measured by difference.

Particle Size

ASTM D1921-89: Particle size (Sieve Analysis) of Plastic Materials

Extractables

To determine the extractables, 1 g of WAM is stirred into 200 g of 0.9% strength by weight sodium chloride solution. The mixture is stirred for 1 hour and then filtered. An aliquot of filtrate is dried to constant weight in a drying oven at about 105–110.degree. C. with gentle air throughput. The extractibles has been determined by weighing the residue, taking into account the sodium chloride content of the solution.

Free Swell Capacity, FSC, (U.S. Pat. No. 6,107,432) FSC-SW (Saline Water)

To determine the FSC, 0.2 g of absorbent product (WAM) (particle fraction 106–850 .mu.m) are weighed into a tea bag measuring 60×0.60 mm, which is then welded. The tea bag is then introduced into an excess of 0.9% strength by weight sodium chloride solution (at least 1.25 l of sodium chloride solution/1 g of WAM). After a swelling time of 20 minutes, the tea bag is removed from the sodium chloride solution and the excess solution is allowed to drip off for 10 minutes. The amount of liquid absorbed by the WAM is then determined by weighing the tea bag.

FSC-SU (Synthetic Urine)

The method of analysis is the same with the difference that the absorbed liquid is synthetic urine with chemical composition: 2.0% urea, 0.9% NaCl, 0.1% MgSO.sub.4, and 0.06% CaCl.sub.2, dissolved in distilled. water.

Centrifuge Retention Capacity,CRC, (U.S. Pat. No. 6,107,432) CRC-SW (Saline Water)

To determine the CRC, 0.2 g of WAM (particle fraction 106–850 .mu.m) are weighed into a tea bag measuring 60×60 mm, which is then welded. The tea bag is then placed in an excess of 0.9% strength by weight sodium chloride solution (at least 1.25 l of sodium chloride solution/1 g of WAM). After a swelling time of 20 minutes, the tea bag is removed from the sodium chloride solution and centrifuged at 250 g for three minutes. The amount of liquid retained by the WAM is determined by weighing the centrifuged tea bag.

CRC-SW (Synthetic Urine)

The method of analysis was the same with the difference being that the absorbed liquid was synthetic urine.

Absorption Under Load, AUL(U.S. Pat. No. 5,712,316).

AUL-SW

The initial weight of powdered superabsorber is placed in a cylinder provided with sieve bottom. The powder is loaded by a piston using a pressure of 80 g/cm$^2$. The cylinder is subsequently placed on a Demand-Absorbency-Tester (DAT), and the superabsorber is allowed to suck 0.9% NaCl-solution for one hour.

AUL-SU

The method of analysis was the same with the difference that the absorbed liquid was the synthetic urine.

Biodegradability(U.S. Pat. No. RE 33,997)

To determine the degree of resistance a material may exhibit to various strains of Pseudomonas aeruginosa, the following experiment is performed on each formulation of hydrogel material. 1 g of WAM is immersed in 100 ml aliquots of nutrient media which has been inoculated with approximately 10$^5$ viable cells per ml. Tubes with WAM particles are incubated at 37° C. and samples are inspected macroscopically each day for changes that may have appeared in edge and surface quality, clarity and gel strength. The experiment is concluded for each sample as soon as any change is observed.

The time elapsed from inoculation with Pseudomonas aeruginosa, in days, until the beginning of the decreasing of the gel strength value, is considered the biodegradability.

EXAMPLE 1

In a 2 liter beaker, equipped with magnetic stirrer there is prepared 1 kg of a solution of reactant A of A4 type, by dissolving 20 g of gelatin, 175 Bloom, from swine (Aldrich, catalog no.27,161-6), cu Mv=85,000 (estimated according to the method of Veis A.—"The Macromolecular Chemestry of Gelatin", Academic Press, New York, 1964), $f_{NN2}$=0.65 10$^{-3}$ moli/g and $f_{COOH}$=1.32 10$^{-3}$ moli/g (values estimated according to Ward A. C., Courtis A.—"The Science and Technology of Gelatin", Academic Press, New York, 1977) in 980 g of water with a conductivity of 4.3 $\mu$S. The solution had a concentration of 2%, represents the liquid L1. Further, in L1 is added 50 g of ammonium hydroxide solution of concentration 5%. The solution resulted (LA) has the pH$^{pp}$= 8.5.

In a reaction vessel of 8 litres, equipped with a stirring rod of anchor type with four blades, thermostatic jacket, condenser, thermometer, dropping funnel and electrode for pH monitoring connected at automated titroprocessor, there is prepared 3862 gram of liquid LB. For this purpose there was introduced in the reaction vessel 80 gram of poly (styrene-alt-maleic anhydride) with Mn=32,000 (ACROS catalog no.17925-2500), as reactant B, 3700 cm$^3$ of ethyl acetate (Aldrich catalog no.11,002-7), 3330 gram OL1, and 300 cm$^3$ N,N'-dimethylformamide (Aldrich catalog no.D15, 855-0), 292 gram OL2. After 30 minutes of homogenization at the temperature of 25° C., by stirring at 100 rpm are added 160 gram water with a conductivity of 4.3 $\mu$S. After another 30 minutes of homogenization under the same conditions one obtains the liquid LB of concentration 2.07%. In dropping funnel are introduced 250 gram of 5% ammonium hydroxide solution and the automated titroprocessor (set for a precision to maintain the pH of system at a constant value of pH$^{pp}$±0.1 pH units) started and there is added the LA. The resulting reaction mass weighs 4867 gram, in which the reactant A4 represents 20%, by weight percent, based on polymeric composite A+B. Then, the reaction mass is stirred at constant speed and temperature which is maintained at the value mentioned above.

The polymer-polymer intercoupling reaction in liquid-liquid heterogeneous system occurs in 150 minutes, and uses 180 gram of 5% ammonium hydroxide solution, until the variation rate of system's pH reached the value $\Delta$pH/$\Delta$t= 0.1/60=0.001667 pH units/minute.

At the end of the chemical reaction the two-phase reaction mass is treated with 22 cm$^3$ of 5% hydrochloric acid to attain a pH=7.5.

After adjusting the pH, the reaction mass is separated by centrifugation with the following technological parameters: a) temperature, not less than 35° C.; b) speed, 2,000 rpm; c) time, 8 minutes. The liquid phase is decanted.

The sediment, weighing $m_G$=198 gram is put in a profiling device of syringe type, formed from a cylinder and a piston, both from polytetrafluoroethylene, equipped with discharging spout with cylindrical section of diameter "$d_F$"=0.8 mm. The profiling syringe is immersed with the discharging zone, into 850 gram acetone, "$m_{NS}$", (ALDRICH catalog no.33, 377-2), under stirring, with a flowing regime Re=15,000 with a spinning flow of gel mass "$D_G$"=50 g/minute.

At the end, the wet granular mass is dried in vacuum at a temperature of 50° C., until there is obtained a dried solid having a moisture content of 5%.

The solid that is obtained after drying is broken up into small pieces in a mill with knifes, to obtain 94.3 grams of granules with an average particles size of 0.25 mm, that represent the water-absorbent material, WAM.

EXAMPLES 2–6

Examples 2–6 for obtaining water-absorbent materials by the method used in example 1 are presented in Table 1.

TABLE 1

| Example | Reagent A | Reagent B | A in RM$^L$, % | OL1:OL2 | pH$^{PP}$ | Reaction time, min |
|---|---|---|---|---|---|---|
| 1 | Gelatin | PSMA[8] | 20 | Eac:DMF 91.94:8.06 | 8.5 | 150 |
| 2 | Starch[1] | PSMA | 40 | Eac:DMF 91.94:8.06 | 8 | 215 |
| 3 | Xanthan[2] | PSMA | 80 | Eac:DMF 91.94:8.06 | 6 | 183 |
| 4 | Chitosan[3] | PSMA | 50 | Eac:DMF 91.94:8.06 | 9 | 128 |
| 5 | SC[4]:CSA[5] 92:8 | PIBMA[9] | 35 | Eac:DMSO 88.54:11.46 | 8 | 307 |
| 6 | Soybean[6]: CMC[7] 25:75 | PEGMA | 60 | Eac:DMSO 88.54:11.46 | 4.5 | 267 |

[1] Starch soluble (ALDRICH, catalog no. 17,993-0);
[2] Gum xanthan (ALDRICH, catalog no. 28,602-8);
[3] Chitosan, average molecular weight(ALDRICH, catalog no. 44,887-7);
[4] Soluble Collagen from Bovine-(ICN catalog no. 193492);
[5] Chondroitin Sulfate A from Bovine Trachea (ICN catalog no. 100237);
[6] Soy protein isolated, protein 92% (ICN catalog no. 905456);
[7] Carboxymethyl cellulose, sodium salt Mw = 250000, DS = 1.2 (ALDRICH, catalog no. 41,928-1);
[8] Poly(styren-alt-maleic anhydride) (ACROS, catalog no. 17925-2500);
[9] Poly(isobutylene-co-maleic anhydride) M$_w$ = 60,000 (ALDRICH, catalog no. 45,904-6).

EXAMPLE 7

In a 2 liter beaker equipped with magnetic stirrer is prepared 1 kg solution of reactant A of A1 type, by dissolving of 60 g of 2-Hydroxyethyl cellulose, Mv 720,000, DS1.5, MS 2.5 (ALDRICH, catalog no.43,497-3,) in 940 g water with a conductivity of 4.3 µS. The resulting solution had a concentration of 6%, representing the liquid L1. To L1 is added 10 g of lithium carbonate solution of concentration 5%. The solution obtained (LA) has a pH$^{PP}$9.

Further processing was as in examples 1–6 with the difference being that as reactant B was used Poly(isoprene-graft-maleic anhydride), PIMA, M$_W$=25.000 (ALDRICH catalog no.45,905-4), as OL1 1,2-dichloroethane (ALDRICH catalog no.D6,156-3), as OL2 dimethyl sulfoxide (ALDRICH catalog no.47,126-7) and the profiling of reaction mass is done in ethyl alcohol (ALDRICH catalog no.36,280-8).

There was obtained 92.8 g of granular product that represents the water-absorbent material, WAM.

EXAMPLES 8–14

The samples of water-absorbent material were tested from the point of view of specific properties for use in diapers. The results obtained are shown in Table 2.

TABLE 2

| Sample | FSC-SW g/g | FSC-SU g/g | CRC-SW g/g | CRC-SU g/g | AUL-SW g/g | AUL-SU g/g | Biodegradation days | Biocompatibility |
|---|---|---|---|---|---|---|---|---|
| Exp1 | 450 | 327 | 398 | 258 | 388 | 259 | 4 | Yes |
| Exp2 | 321 | 288 | 306 | 257 | 262 | 244 | 3 | Yes |
| Exp3 | 215 | 198 | 148 | 106 | 98 | 45 | 1.5 | Yes |
| Exp4 | 147 | 128 | 131 | 119 | 110 | 92 | 3 | Yes |
| Exp5 | 402 | 375 | 358 | 317 | 259 | 204 | 5 | Yes |
| Exp6 | 382 | 271 | 255 | 178 | 295 | 208 | 2 | Yes |
| Exp7 | 228 | 157 | 195 | 129 | 87 | 59 | 4 | Yes |

We claim:

1. A bio-compatible, biodegradable macromolecular water-absorbent polymeric material having a three-dimensional configuration with intermolecular covalent bonds and containing free functional groups selected from OH, SH, $NH_2$, and COOH, said polymer being formed by polymer-polymer inter-coupling interaction between a natural water-soluble polymer A or its derivatives having a molecular weight between 20,000 and 500,000 Da, and a synthetic polymer B in a ratio of A:B of 15:85 to 85:15, wherein the natural polymer A is selected from the group consisting of:

A1)—non-ionic natural, partially denatured or chemically modified polymer, that does not dissociate in water and which can undergo polymer-polymer intercoupling reactions, having only free hydroxyl groups in an amount of at least $5 \times 10^{-3}$ moles OH/g, and optionally containing non-ionic groups, A2)—anionic natural, partially denatured or chemically modified polymer, that dissociates in water to form anions and which can undergo polymer-polymer intercoupling reactions, said polymer optionally containing non-ionic groups, A3)—cationic natural, partially denatured or chemically modified polymer, that dissociates in water to form cations and which can undergo polymer-polymer intercoupling reactions, said polymers optionally containing non-ionic groups, A4)—amphoteric natural, partially denatured or chemically modified polymer, that dissociates in water to form both anions and cations and which can undergo polymer-polymer intercoupling reactions, and A5)—mixtures of A1–A4, polymer A being capable of undergoing polymer-polymer intercoupling, and wherein:

the synthetic polymer B is a linear or branched reactive synthetic copolymer having a molecular weight of 10,000–500,000 Da derived from a vinyl monomer and an ethylenically unsaturated monomer, said copolymer having a backbone with polymeric subunits $R_n$ and $R_r$ wherein R represents a subunit covalently bonded to the polymer backbone, n represents non-reactive chemical functional groups and r represents reactive chemical functional groups.

2. The polymeric material as in claim 1, wherein the natural polymer is of the type A2, having free carboxyl groups in an amount at least $1 \times 10^{-3}$ moles COOH/g, and optionally containing non-ionic groups.

3. The polymeric material as in claim 1, wherein the natural polymer is of the type A3, forming in water ammonium groups having at least $0.5 \times 10^{-3}$ moles $NH_2$/g, and optionally containing non-ionic groups.

4. The polymeric material as in claim 1, wherein the natural polymer is of the type A4, forming in water anions and cations ($COO^-$ and $NH_4^+$) with at least $1 \times 10^{-3}$ moles $COO^-$/g, and at least $0.5 \times 10^{-3}$ moles $NH_4^+$/g, with an isoelectric point not less than 2.5 and not more than 10.5, and optionally containing non-ionic groups.

5. The polymeric material as in claim 1, wherein the natural polymer A is a mixture of at least two polymers selected from the group consisting of A1, A2, A3, and A4 and each polymer is present at least to the amount of 1%.

6. The polymeric material as in claim 1, derived from N polymers (N=2, 3 or 4), which participate in the polymer-polymer intercoupling, wherein K polymers (K=1, 2 or 3) are selected from the group consisting of biopolymers A as defined in claim 1, and N minus K polymers are selected from the group consisting of polymers B as defined in claim 1.

7. The polymeric material as in claim 1, wherein the natural polymer is selected from the group consisting of proteins, glycoproteins, polysaccharides or proteoglycans of animal, vegetal or bactenal origins, and their derivatives.

8. The polymeric material as in claim 1, wherein the natural polymer is selected from the group consisting of starch, amylose, dextran, chitin, pullulan, gellan gum, xylan, galactomannan, carrageenan, agar, locust bean gum, guar gum, gum arabic, pectin, methylcellulose, ethylcellulose, hydroxyethylcellulose, hydroxypropyl-cellulose, ethylhydroxyethylcellulose, hydroxybutylmethylcellulose, hydroxyethylmethylcellulose, hydroxyethyl starch, hydroxypropyl starch, alginate, xanthan, hyaluronic acid, heparin, chondroitin sulfate, keratan, dermatan, oxidized cellulose, carboxymethylcellulose, carboxymethyl starch, chitosan, and polysaccharides having glycosamine residues in natural or diacetylated form.

9. The polymeric material as in claim 1, wherein the natural polymer is selected from collagen, collagenic biopolymers from terrestrial and marine origin and their derivatives, alfa-keratose, gama-keratose, keratin hydrolysates, derivatives of the elastinic biopolymers, fibrin and derivatives, fibroin and derivatives, ovalbumine, bovine serumalbumine and albumine derivatives, casein and its derivatives, soybean protein and its derivatives, heparosan, hyalurosan, and diacetylated glycosaminoglycans.

10. The polymeric material as in claim 1, wherein the polymer B is a linear or branched polymer obtained by a single stage polyreaction or in two stages, by a polyreaction followed by chemical modification.

11. The polymeric material as in claim 10, wherein R may include a reactive $R_r$ or non-reactive $R_n$ chemical function.

12. The polymeric material as in claim 10, wherein R may include a spacer group interposed between the chemical function and the chain that is anchored to it.

13. The polymeric material as in claim 12, wherein the spacer group is selected from the group consisting of $—COO^-$ and $—(CH)_n—$ with n equals 1–4.

14. The polymeric material as in claim 1, wherein the reactive chemical functions of synthetic polymer B are ionic reactive chemical functions $R_r$ selected from the group consisting of $—CO—O—CO—$ and $—CO—NH—CO—$.

15. The polymeric material as in claim 14, wherein the reactive chemical function is selected from the group consisting of maleic anhydride, itaconic anhydride, citraconic anhydride, 2-octenylsuccinic anhydride and corresponding imides.

16. The polymeric material as in claim 1, wherein the ionic reactive chemical functionality of polymer B, is symbolized as $f_r^B$, and is in the range $5 \times 10^{-3}$ to $1 \times 10^{-2}$ "r"/g.

17. The polymeric material as in claim 14, wherein the non-reactive chemical functions $R_n$ can comprise m number of groups (m=1–4) selected from the group consisting of hydrogen, aliphatic or aromatic hydrocarbon residues with from 1 to 20 carbon atoms, non-active ester, ether or imino groups, and non-active halogen derivatives.

18. The polymeric material as in claim 17, wherein the non-reactive chemical functions $R_n$ may partially include polar chemical groups selected from the group consisting of hydroxyl, amino, amido, and carboxylic groups.

19. The polymeric material as in claim 17, wherein the non-reactive substituents of the polymer B are attached to the backbone of the copolymer, that represents monomer residues.

20. The polymeric material as in claim 17, wherein the synthetic polymer B is prepared from monomers with non-reactive groups selected from the group consisting of styrenes, vinyl-toluene, vinyl esters of saturated $C_1$–$C_4$-carboxylic acids, alkyl vinyl ethers with at least 2 carbon atoms in the alkyl group, acrylic and methacrylic esters, conjugated diolefins, allenes, olefin halides, ethylene, propene, isobutylene, butadiene, isoprene, esters of mono-ethylenically unsaturated $C_3$–$C_6$-carboxylic acids, N-vinyllactams, acrylic and methacrylic esters of alkoxylated monohydric saturated alcohols, vinyl pyridine and vinyl morpholine, N-vinylformamide, dialkyldiallylammonium halides, N-vinylimidazoles and N-vinylimidazolines, acrylamide, methacrylamide, and acrylonitryl.

21. The polymeric material as in claim 17, wherein the synthetic polymer B is prepared from ethylene, propene, styrene, isobutylene, vinyl acetate, methyl acrylate, methyl methacrylate, acrylamide, vinylether, N-vinylpyrrolidone, acrylic acid, methacrylic acid or maleic acid.

22. The polymeric material as in claim 17, wherein the synthetic polymer B is prepared from pharmaceutically accepted monomers selected from the group consisting of poly-(ethylene-alt-maleic anhydride), poly-(ethylene-graft-maleic anhydride), poly-(isobutylene-co-maleic anhydride), poly-(isoprene-graft-maleic anhydride), poly-(maleic anhydride-co-1-octadecene), poly-(propylene-graft-maleic anhydride), and poly-(styrene-co-maleic anhydride).

23. A process for preparing a bio-compatible biodegradable macromolecular water absorbent polymeric material as in claim 1, comprising reacting a natural polymer A with a polymer B by intercoupling in a liquid-liquid heterogeneous system in the absence of any cross-linking or coupling agent.

24. A process for preparing a bio-compatible biodegradable macromolecular water absorbent polymeric material as in claim 1, comprising the folloeing steps:
  a. preparing a 1–20% aqueous solution of polymer or mixed polymers A, referred to as L1, adjusting the pH to between 7.5 and 9.5 with basic aqueous solution (L3), the adjusted solution referred to as LA,
  b. preparing a 1–20% organic solvent solution of polymer B, referred to as L2, mixing said solution with water to a ratio of between 90:10 to 99:1 respectively, this organic-aqueous solution referred to as LB,
  c. homogenizing solution LB at a temperature between 15° C. and 35° C. and adjusting the pH with solution L3 via a dropping funnel,
  d. adding in a kneader a quantity of solution LA for heterogeneous polymer-polymer intercoupling in an amount so that polymer A will constitute between 15% and 85% of the polymer material while maintaining the system's pH at a constant value of $pH^{pp}=\pm 0.1$ pH units,
  e. separating and recovering the product from the reaction mass.

25. The process as in claim 24, wherein the solvent for solution L2 is a mixture of organic solvents $OL_1$ and $OL_2$ at a ratio of 85:15 to 100:0, where $OL_1$ has a water solubility of between $10^3$ ppm and $10^5$ ppm and is selected from the group consisting of ethyl acetate, dichloromthane, 1,2-dichloroethane, methylchloride, 1,1,1-trichloroethane, and trichloroethylene, and $OL_2$ is an aprotic polar solvent selected from the group consisting of DMF, DMA, and DMSO.

26. The process as in claim 23, wherein the polymer-polymer intercoupling reaction in the liquid-liquid heterogeneous system is performed until the variation rate of the system's pH attains the value $\Delta pH/\Delta t=0.1/60=0.001667$ pH units/minute.

27. The biocompatible, biodegradable, highly water absorbent material as in claim 1 for use in personal care products that absorb body fluids.

28. The material as in claim 1 for use in baby diapers, incontinence products and feminine hygiene products.

29. The biocompatible, biodegradable, highly water absorbent material as in claim 1 for use in soil conditioning.

30. The biocompatible, biodegradable, highly water absorbent material as in claim 1 for use as drying agents of hydrophobic liquids such as petroleum products or fuels.

31. The biocompatible, biodegradable, highly water absorbent material as in claim 1 for use in medical biomaterials.

* * * * *